United States Patent
Wilson et al.

(10) Patent No.: US 6,727,221 B1
(45) Date of Patent: Apr. 27, 2004

(54) PERFUME COMPOSITION

(75) Inventors: Craig S. Wilson, Kent (GB); Tony Minhas, Kent (GB); John M. Behan, Kent (GB); Alan F Provan, Kent (GB)

(73) Assignee: Quest International B.V., Naarden (NL)

(*) Notice: Subject to any disclaimer, the term of this patent is extended or adjusted under 35 U.S.C. 154(b) by 0 days.

(21) Appl. No.: 09/743,111

(22) PCT Filed: Jun. 6, 1999

(86) PCT No.: PCT/GB99/02013

§ 371 (c)(1),
(2), (4) Date: Jan. 5, 2001

(87) PCT Pub. No.: WO00/01352

PCT Pub. Date: Jan. 13, 2000

(30) Foreign Application Priority Data

Jul. 7, 1998 (GB) ............................................. 9814648

(51) Int. Cl.⁷ ................................................. A61K 7/46
(52) U.S. Cl. ......................................... 512/1; 424/76.8
(58) Field of Search ............................. 512/1; 424/76.8

(56) References Cited

U.S. PATENT DOCUMENTS

| | | |
|---|---|---|
| 3,945,950 A | 3/1976 | Vosganiantz |
| 4,548,821 A | 10/1985 | Hall et al. |
| 5,260,053 A | 11/1993 | Chappell et al. ............... 424/65 |
| 5,554,588 A | 9/1996 | Behan et al. |
| 5,874,070 A | 2/1999 | Trinh et al. |

FOREIGN PATENT DOCUMENTS

| | | |
|---|---|---|
| DE | 44 11 664 | 10/1995 |
| EP | 480 520 | 4/1992 |
| EP | 731 160 | 9/1996 |
| WO | WO 89/00042 | 1/1989 |
| WO | WO 96/12467 | 5/1996 |
| WO | WO 98/50011 | 11/1998 |

OTHER PUBLICATIONS

Morris et al: "Antimicrobial Activity of Aroma Chemicals and Essential Oils", Journal of the American Oil Chemists' Society May 1, 1979, pp. 595–603, XP000645444, ISSN:, 0003–021X, PG 595, para 1–para 3, table III.

*Primary Examiner*—Jill Warden
*Assistant Examiner*—Monique T. Cole
(74) *Attorney, Agent, or Firm*—Morgan, Lewis & Bockius LLP

(57) ABSTRACT

A perfume composition contains at least 30% by weight of perfume components having a minimum inhibitory concentration (MIC) for coryneform bacteria of greater than 0.1%. The composition can be used in deodorant products to reduce body malodour sub-lethally, i.e. without significantly affecting the numbers of bacteria present on the skin surface.

5 Claims, No Drawings

PERFUME COMPOSITION

The invention relates to a perfume compositon containing perfume component(s) which is capable of sub-lethally reducing or preventing body malodour produced from perspiration moisture materials by members of the skin microflora, ie without killing significant numbers of the bacteria present on the skin surface.

Body odour results from the microbial transformation of organic molecules both simple and complex which are constituents of sweat. As well as the pungent undesirable odour that is produced by these reactions some of the by-products may, in some cases cause irritation to the skin.

It has been suggested in the prior art that body odour can be reduced by using various different materials, for example;
1) Astringent agents such as aluminium salts e.g. aluminium chlorohydrate. These components work by reducing or stopping the secretion of perspiration. However these actives denaturize skin proteins, and may alter the thermal balance of the armpit.
2) The topical application of antimicrobial substances to the skin. Bactericidal agents e.g. ethanol are a non specific mechanism of controlling body odour which as a result kill without any degree of discrimination of the microorganisms present on the skin. Organisms that are not responsible for malodour are killed to the same extent or worse than their malodorous counterparts.
3) Perfumes may be applied to mask the odour, but new generation perfumes have been disclosed which exhibit an active deodorant effect on the underarm skin flora. EP-B-3172, EP-A-5618, U.S. Pat. No. 4,304,4679, U.S. Pat. No. 4,322,308, U.S. Pat. No. 4,278,658, U.S. Pat. No. 4,134,838, U.S. Pat. No. 4,288,341 and U.S. Pat. No. 4,289,641 all describe perfume compositions which exhibit a deodorant action when applied to human skin, or when included in a laundry product used to launder textiles.

The present generation of deodorants offer protection against body malodour by reducing the numbers of the bacterial microflora considerably without any degree of selective discrimination.

Coryneform bacteria found on human skin have been shown to carry out the incomplete biotransformation of organic molecules secreted in human sweat. Leyden. J. J. et al, "The microbiology of human axilla and its relationship to axillary odour", J. of Invest. Derm., 77(1981), 413–416. Coryneform bacteria have also been shown to be responsible for the production of various odorous metabolites. J. Soc. Cosmet. Chem., 34 (1982), 193–202.

The present invention is directed to a perfume composition and the use thereof to retard or inhibit the production of malodorous compounds produced, for example by coryneform bacteria present on the skin surface, preferably without killing significant numbers of the bacteria, and/or other members of the skin microflora.

Accordingly, the present invention provides a perfume composition comprising at least 30% by weight of perfume components having a minimum inhibitory concentration (MIC) for coryneform bacteria of greater than 0.1%.

The invention further provides a perfume composition comprising at least 30% by weight of one or more of the following perfume components: (Z)-3,4,5,6,6-pentamethylhept-3-en-2-one, 2,6,10-trimethylundec-9-enal, 1-(4-Methoxyphenyl)-1-propene, diethylcyclohex-2-en-1-one, dimethyl cyclohex-2-en-1-one, Basil comores, 2-methyl-5-(1-methyl-1-ethenyl)-2-cyclohexen-1-one, Cis-3-hexenyl salicylate, methyl 3,3-dimethylbicyclo(2.2.1) heptane-2-carboxylate, Citronellol, Corriander, 2-methyl-3-(4-(1-methylethyl)phenyl)propanal, 1-(2,6,6-trimethyl-1,3-cyclohexadienyl)-2-buten-1-one, Dihydrojasmone, alpha, alpha-Dimethylphenylethylacetate, Dimethyl anthranilate, 1-(2-((1-(ethyloxy)ethyl)oxy)ethyl)benzene, 4-(4-methyl-3-pentenyl)cyclohex-3-ene-1-carbaldehyde, 3-(4-methyl-3-pentenyl)cyclohex-3-ene-1-carbaldehyde), Firneedle, 3-(1,3-benzodioxol-5-yl)2-methylpropanol, α-ionone, β-ionone, tricyclo[5.2.1.0 2,6]dec-4-en-8-yl ethanoate, Jasmopyrane forte, 1-methoxy-4-(2-propenyl)-benzene, 2-(1,1-dimethylethyl)cyclohexyl ethanoate), PTBCHA, 2,4-dimethyl-4-phenyltetrahydrofuran, 4-Methyl-2-(2-methylprop-1-enyl)tetrahydropyran, Rosemary Tunisian, 3,6-dihydro-2-phenyl-4-methyl-2H-pyran, Terpinolene extra, Tetrahydro linalol, Thyme white, Ti-tree pure, and Undecalactone gamma.

The invention also provides a cosmetic method for reducing or preventing body malodour by topically applying to human skin a perfume composition comprising at least 30% by weight of perfume components having a minimum inhibitory concentration (MIC) for coryneform bacteria of greater than 0.1%.

The invention also provides a deodorant product comprising a perfume composition defined herein.

The invention also provides the use of a perfume composition, comprising at least 30% by weight of perfume components having a minimum inhibitory concentration (MIC) for coryneform bacteria of greater than 0.1%, to reduce body malodour.

The invention still further provides the use of a deodorant product, comprising a perfume composition which comprises at least 30% by weight of perfume components having a minimum inhibitory concentration (MIC) for coryneform bacteria of greater than 0.1%, to reduce body malodour.

Coryneform is a designation of a large ill-defined group of bacteria. The diverse genera that have been included with the coryneforms include Actinomyces, Arachnia, Arcanobacterium, Arthrobacter, bacterionema, Bifidobacterium, Brevibacterium, Cellulomonas, Corynebacterium, Eyrsipelothrix, Eubacterium, Kurthia, Listeria, Mycobacterium, Nocardia, Oerskovia, Propionibacterium, Rhodococcus and Rothia.

The term "perfume component" is used herein to represent a material which is added to a perfume to contribute to the olfactive properties of the perfume. A perfume component can be acceptably employed to provide odour contributions to the overall hedonic performance of products. Typically, a perfume component will be generally recognised as possessing odours in its own right, will be relatively volatile and often has a molecular weight within the range 100 to 300. Typical materials which are perfume components are described in "Perfume and Flavour Chemicals", Volumes I and II (Steffan Arctander, 1969). A perfume composition will contain a number of individual perfume components, and optionally a suitable diluent. The concentration of perfume components referred to herein is relative to the total concentration of perfume components present in the composition, ie excludes any diluent.

The perfume composition according to the present invention preferably comprises at least 40%, more preferably at least 50%, particularly at least 60%, and especially at least 70% by weight of perfume components having a minimum inhibitory concentration (MIC) for coryneform bacteria, preferably for *Corynebacteria xerosis* as measured in Example 1 below, of greater than 0.1%. The preferred perfume components preferably have an MIC greater than 0.25%, more preferably geater than 0.5%, and also suitably have an MIC of less than 10%, preferably less than 5%, more preferably less than 3%, particularly less than 2%, and especially less than 1%.

The preferred perfume components have been shown to be capable of a significant deodorant action when used at concentrations below their MIC for coryneform bacteria. The preferred components may be added to other perfume components to deliver perfumes with the desired deodorant and hedonistic properties. The perfume composition suitably comprises up to 70%, preferably up to 60%, more preferably up to 50%, particularly up to 40%, and especially up to 30% by weight of perfume components having an MIC for coryneforn bacteria outside of the above preferred ranges. A perfume composition according to the present invention surprisingly provides a perfume with high deodorant activity, but measurably lower anti-microbial effects, particularly against coryneform bacteria. The perfume composition preferably provides deodorant activity without killing significant numbers of the coryneform bacteria, and/or other types of skin bacteria.

A preferred perfume composition yields, an Odour Reduction Value, measured as described in Example 3, of at least 10%, more preferably at least 30%, and particularly at least 50%.

A perfume composition according to present invention may be used in deodorant products which include body deodorants and antiperspirants such as roll ons, gel products, stick deodorants, antiperspirants, shampoos, soaps, shower gels, talcum powder, hand creams, skin conditioners, sunscreens, sun tan lotions, skin and hair conditioners. The perfume composition may also be used in other product areas to deliver a degree of deodorant protection, for example in laundry and household products such as rinse conditioners, household cleaners and detergent cleaners. The provision of deodorant protection may also be provided in textiles themselves by the incorporation of these perfume compositions during production, using techniques known in the art. A deodorant product preferably comprises at least 0.05% to 4%, more preferably 0.1% to 2% by weight of perfume components having a minimum inhibitory concentration (MIC) for coryneform bacteria of greater than 0.1%, more preferably selected from the list below.

Suitable perfume components, for use in a perfume composition according to the present invention, include the following materials.

Acetyl di iso amylene ((Z)-3,4,5,6,6-pentamethylhept-3-en-2-one)
Adoxal (2,6,10-trimethylundec-9-enal)
Anethole synthetic (1-(4-Methoxyphenyl)-1-propene)
Azarbre (mixture of diethyl and dimethylcyclohex-2-en-1-one)
Basil comores
Carvone laevo (2-methyl-5-(1-methyl-1-ethenyl)-2-cyclohexen-1-one)
Cis-3-hexenyl salicylate
Cistulate (methyl 3,3-dimethylbicyclo(2.2.1)heptane-2-carboxylate)
Citronellol
Corriander
Cyclamen aldehyde (2-methyl-3-(4(1-methylethyl)phenyl) propanal)
Damascenone (1-(2,6,6-trimethyl-1,3-cyclohexadienyl-2-buten-1-one)
Dihydrojasmone
Dimethyl Benzyl Carbinyl acetate (alpha,alpha-Dimethylphenylethylacetate)
Dimethyl anthranilate
Efetaal (1-(2-((1-(ethyloxy)ethyl)oxy)ethyl)benzene)
Empetaal (mixture of 4-(4-methyl-3-pentenyl)cyclohex-3-ene-1-carbaldehyde) and 3-(4-methyl-3-pentenyl) cyclohex-3-ene-1-carbaldehyde))
Fir needle
Helional (3-(1,3-benzodioxol-5-yl)-2-methylpropanol)
Ionone (mixture of $\alpha$ and $\beta$ isomers)
Jasmacyclene (tricyclo[5.2.1.0 2,6]dec-4-en-8-yl ethanoate)
Jasmopyrane forte
Methyl chavicol (1-methoxy-4-(2-propenyl)benzene)
Ortholate (2-(1,1-dimethylethyl)cyclohexyl ethanoate)
PTBCHA
Rhubafuran (2,4-dimethyl-4-phenyltetrahydrofuran)
Rose Oxide Racemic (4-Methyl-2-(2-methylprop-1-enyl) tetrahydropyran)
Rosemary Tunisian
Rosyrane (3,6-dihydro-2-phenyl-4-methyl-2H-pyran)
Terpinolene extra
Tetrahydro linalol
Thyme white
Ti-tree pure
Undecalactone gamma A preferred perfume composition comprises at least 5, more preferably at least 10, and particularly at least 18 of the above perfume components.

The invention is illustrated by the following examples.

EXAMPLE 1

Standard Assessment of MIC

A fresh culture of the test inoculum (*Corynebacteria xerosis* NCTC 7243 (National Collection of Type Cultures, Public Health Laboratory Service, Central Public Health Laboratory, 61 Colindale Avenue, London)) (redeposited on 22 Jul. 1999 under the Budapest Treaty as NCIMB 41021 (National Collections of Industrial and Marine Bacteria Ltd, 23 St Machar Drive, Aberdeen Scotland) diluted in sterile 0.1% special peptone solution to give a concentration of approximately $10^5$ cfu/ml was prepared.

Test samples were diluted in sterile trptone soya broth (TSB) Each row of the microtitre plate (labelled A–H) was allocated to one sample, i.e. eight samples per plate. Row 8 (H) contained only TSB for use as a bacterial control to indicate level of turbidity In the absence of test material. Aseptically 200 $\mu$l of the initial dilution was transferred to the 1st and 7th well of the appropriate row. All other test wells were filled with 100 $\mu$l of sterile TSB using an 8 Channel pipette. The contents of all wells in column 1 were mixed by sucking samples up and down pipette tips before 100 $\mu$l was transferred to column 2. The same sterile pipette tips can be used to transfer 100 $\mu$l of each well in column 7 in to the appropriate well in column 8. Tips were discarded into disinfectant solution. Using fresh sterile tips the process was repeated by transferring 100 $\mu$l from column 2 into column 3 (and 8 into 9). The process was continued until all wells in columns 6 and 12 contained 200 $\mu$l. After mixing 100 $\mu$l was discarded from wells in these columns to waste.

To all wells 100 $\mu$l of pre-diluted test culture was added giving 200 $\mu$l final volume in each well.

A blank plate was prepared for each set of samples using the above protocol except 100 $\mu$l of sterile 0.1% peptone was added instead of bacterial culture.

Plates were sealed using autoclave tape and incubated overnight at 35° C.

The reader was preset to gently agitate the plates to mix the contents before reading absorbance at 540 nm. The control plate for each set of samples was read first. The reader was then reprogrammed to use the control readings to blank all other plate readings of the set of test materials (i.e. removing turbidity due to perfume and possible colour changes during incubation) thus only printing out absorbances due to turbidity resulting from bacterial growth. Limits were set so that degrees of turbidity were given a rating.

The MIC was taken as the level of sample required to inhibit growth completely (change in absorbance<0.2).

EXAMPLE 2

Perfume Formulations

| Ingredient | % by Weight | |
|---|---|---|
| | Perfume X | Perfume Y |
| Acetyl di iso amylene | 7 | 5.8 |
| Adoxal | | 0.4 |
| Amberlyn super PM577 | 4 | |
| Azarbre | 4 | |
| Benzyl acetate extra | 8 | |
| Benzyl salicylate | 6.5 | 6.7 |
| Cassis base 345 AB2967 | | 4.2 |
| Cis-3-hexenyl salicylate | | 2.5 |
| Citral lemarome | | 0.7 |
| Citronellol pure | | 14.2 |
| Cyclamen aldehyde | | 4.2 |
| Dihydro Eugenol | 1.5 | |
| Dihydro Jasmone | 0.7 | |
| Dimethyl benzyl carbinyl acetate | 3 | |
| Diphenyl methane | 2 | |
| Dupical | | 0.4 |
| Empetal | 0.4 | 0.5 |
| Geraniol pure | 7 | 8 |
| Helional | | 4.2 |
| Ionone | 12.5 | |
| Jasmacyclene | 2.2 | 2.5 |
| Ligustral | 0.3 | |
| Ligustral 10% DPG AA 1488 | 2.5 | |
| Lyral | 8 | 12.5 |
| Methyl iso eugenol | 4 | |
| Methyl octyl acetaldehyde 10% DPG | | 1.7 |
| Orange terpenes | | 0.3 |
| Ortholate | | 6.7 |
| Para cresyl methyl ether | 10.4 | |
| Para tert butyl cyclo hexyl acetate | 10 | |
| Phenyl ethyl alcohol | 10 | 10.6 |
| Roseacetone | 6 | 10.6 |
| Perfume Z | | |
| Adoxal DEP AA022 | 4 | |
| Benzyl acetate extra | 7.5 | |
| Benzyl salicylate | 8 | |
| Cardamon ceylon A pure | 2 | |
| Cassis base 345 AB 2967 | 2 | |
| Cis 3 hexenyl salicylate | 5 | |
| Citronellol pure | 12 | |
| Cyclamen aldehyde | 2 | |
| Dimethyl Benzyl Carbinyl Acetate | 2 | |
| Geraniol pure | 8 | |
| Helional | 2 | |
| Ionone | 6 | |
| Ligustral | 0.3 | |
| Lily aldehyde | 6 | |
| Lyral | 10 | |
| Mandarinal 32048 SAE | 4 | |
| Methyl iso eugenol | 3 | |
| methyl octyl acetaldehyde | 2.8 | |
| ortholate | 3 | |
| Para cresyl methyl ether | 0.4 | |
| Phenyl ethyl alcohol | 5 | |
| Roseacetone | 5 | |

EXAMPLE 3

The following are typical formulations of deodorant products which are made by methods common in the art.

Deodorant Sticks

| | Content (% by weight) | |
|---|---|---|
| Ingredient | Formulation 1A | Formulation 1B |
| Ethanol | | 8 |
| Sodium Stearete | 7 | 6 |
| Propylene glycol | 70 | 12 |
| Perfume | 1.5 | 2 |
| PPG-3 Myristyl ether | | 28 |
| PPG-10 Cetyl ether | | 10 |
| Clyclomethicone | | 34 |
| Silica | | |
| Water | 21.5 | |

Aerosols

| | content (% by weight) | |
|---|---|---|
| Ingredient | Formulation 2A | Formulation 2B |
| Ethanol B | up to 100 | |
| Propylene glycol | as required | |
| Perfume | 2.5 | 1.5 |
| Chlorhydrol microdry | | 31.8 |
| Silicone Fluid DC344 | | up to 100 |
| Bentone gel IPP | | 13.65 |
| Irgasan DP300 | 0.03 | |
| Dimethyl ether | 20 | |
| Concentrate | | 22 |
| Water | 23 | |

Roll ons

| | Content (% by weight) | |
|---|---|---|
| Ingredient | Formulation 3A | Formulation 3B |
| Ethanol | to 100% | 60 |
| Klucel MF | | 0.65 |
| Cremphor RM410 | | 0.5 |
| erfume | 0.5 | 1 |
| AZTC* | 20 | |
| Clyclomethicone | 68 | |
| Dimethicone | 5 | |
| Silica | 2.5 | |
| Water | | 37.85 |

*Aluminium zirconium tetrachlorohydro glycinate

The three perfume compositions of Example 2 were made and tested for deodorant action in an underarm product, using an Odour Reduction Value test generally as described in U.S. Pat. No. 4,278,658, but with the substitution of the perfumed soap by perfumed roll-on product, using the formulation described in Formulation 3B.

The Odour Reduction Value test was carried out using a panel of 40 Caucasian male subjects. A standard quantity (approximately 0.4 g) of a roll-on product containing one of the perfume compositions or an unperfumed control was applied to the axillae of the panel members in accordance with a statistical design.

After a period of five hours the axillary odour was judged by three trained female assessors who scored the odour intensity on the 0 to 5 scale, as shown below

| Score | Odour level | Conc. of aqueous isovaleric acid (ml/l) |
|---|---|---|
| 0 | No odour | 0 |
| 1 | Slight | 0.013 |
| 2 | Definite | 0.053 |
| 3 | Moderate | 0.22 |
| 4 | Strong | 0.87 |
| 5 | Very Strong | 3.57 |

Average scores for each test product and the control product were then determined and the score for each test product was subtracted from the score for the control product to give the Odour Reduction Value.

| | |
|---|---|
| Average panel score perfume Y | 1.57 |
| Control panel score | 2.41 |
| Odour Reduction Value perfume | 0.74 |
| Odour Reduction Value as percentage of control score | 31% |
| Difference for significance @95% | 0.24 |
| Difference for significance @99% | 0.32 |
| Average panel score perfume X | 1.91 |
| Control panel score | 2.41 |
| Odour Reduction Value perfume | 0.5 |
| Odour Reduction Value as percentage of control score | 21% |
| Difference for significance @95.% | 0.24 |
| Difference for significance @99% | 0.32 |
| Average panel score perfume Z | 2.05 |
| Control panel score | 2.41 |
| Odour Reduction Value perfume | 0.36 |
| Odour Reduction Value as percentage of control score | 15% |
| Difference for significance @95% | 0.24 |
| Difference for significance @99% | 0.32 |

The perfume composition referred to as X and Y had at least 40% by weight of specific perfume components listed on page 4 above, present, whilst the perfume referred to as Z had at least 30% of such components. Perfume X contained 40%, Y 41%, and Z 34% by weight of perfume components having a minimum inhibitory concentration (MIC) for coryneform bacteria of greater than 0.1%.

What is claimed is:

1. A cosmetic method for reducing or preventing body malodour by topically applying to human skin a perfume composition comprising at least 30% by weight of perfume components having a minimum inhibitory concentration (MIC) for coryneform bacteria of greater than 0.1%, wherein the perfume components are selected from one or more of the following: (Z)-3,4,5,6,6-pentamethylhept-3-en-2-one, 2,6,10-trimethylundec-9-enal, 1-(4-Methoxyphenyl) 1-propene, diethylcyclohex-2-en-1-one, dimethylcyclohex-2-en-1-one, Basil comores, 2-methyl-5-(1-methyl-1-ethenyl)-2-cyclohexen)-1-one, Cis-3-hexenyl, salicylate, methyl 3,3-dimethylbicyclo(2.2.1)heptane-2-carboxylate, 2-methyl-3-(4-(1-methylethyl)phenyl)propanal, 1-(2,6,6-methyl-1,3-cyclohexadienyl)-2-buten-1-one, Dihydrojasmone, alpha,alpha-Dimethylphenylethylacetate, Dimethyl anthranilate, 1-(2-((1-(ethyloxy)ethy)oxy)ethyl) benzene; 4-(4-methyl-3-pentenyl)cyclohex-3-one-1-carbaldehyde, 3-(4-methyl-3-pentenyl)cyclohex-3-ene-1-carbaldehyde), Fir needle, 3-(1,3-benzodioxol-5-yl)-2-methylpropanol, α-ionone, β-ionone, tricyclo[5.2.1.0 2,6] and dec-4-en-8-yl ethanoate, Jasmopyrane forte, 1-methoxy-4-(2-propenyl)-benzene, 2-(1,1-dimethylethyl)cyclohexyl ethanoate), PTBCHA, 2,4-dimethyl-4-phenyl (tetrahydrofuran, 4-Methyl-2-(2-methylprop-1-enyl) tetrahydropyran, Rosemary Tunisian, 3,6-dihydro-2-phenyl-4-methyl-2H-pyran, Terpinolene extra, Tetrahydro linalol, Thyme white, Ti-tree pure, and undecalactone gamma.

2. A method according to claim 1 which yields an Odour Reduction Value of at least 10%.

3. A method according to claim 1 wherein the biotransformation by coryneform bacteria, of organic molecules present in human sweat is diminished sub-lethally.

4. A cosmetic method for reducing or preventing body malodour by topically applying to human skin a perfume composition comprising at least 50% by weight of perfume components having a minimum inhibitory concentration (MIC) for coryneform bacteria of greater than 0.1%, wherein the perfume components are selected from one or more of the following: (Z)-3,4,5,6,6-pentamethylhept-3-en-2-one, 2,6,10-trimethylundec-9-enal, 1-(4-Methoxyphenyl)-1-propene, diethylcyclohex-2-en-1-one, dimethylcyclohex-2-en-1-one, Basil comores, 2-methyl-5-(1-methyl-1-ethenyl)-2-cyclohexen-1-one, Cis-3-hexenyl salicylate, methyl 3,3-dimethylbicyclo(2.2.1)heptane-2-carboxylate, Citronellol, 2-methyl-3-(4-(1-methylethyl)phenyl)propanal, 1-(2,6,6-trimethyl-1,3-cyclohexadienyl)2-buten-1-one, Dihydrojasmone, alpha,alpha-Dimethylphenylethylacetate, Dimethyl anthranilate, 1-(2-((1-(ethyloxy)ethyl)oxy)ethyl) benzene, 4-(4-methyl-3-pentenyl)cyclohex-3-ene-1-carbaldehyde, 3-(4-methyl-3-pentenyl)cyclohex-3-ene-1-carbaldehyde), Fir needle, 3-(1,3-benzodioxol-5-yl)-2-methylpropanol, α-ionone, β-ionone, tricyclo[5.2.1.0 2,6] dec-4-en-8-yl ethanoate, Jasmopyrane forte, 1-methoxy-4-(2-propenyl)-benzene, 2-(1,1-dimethylethyl)cylohexyl ethanoate), PTBCHA 2,4-dimethyl-4-phenyltetrahydrofuran, 4-Methyl-2-(2-methylprop-1-enyl) tetrahydropyran, Rosemary Tunisian, 3,6-dihydro-2-phenyl-4-methyl-2H-pyran, Terpinolene extra, Tetrahydro linalol, Thyme white, Ti-tree pure, and Undecalactone gamma.

5. A cosmetic method for reducing or preventing body malodour by topically applying to human skin a perfume composition comprising at least 30% by weight of at least 5 perfume components having a minimum inhibitory concentration (MIC) for coryneforn bacteria of greater than 0.1%, wherein the perfume components are selected from one or more of the following: (Z)-3,4,5,6,6-pentamethylhept-3-en-2-one, 2,6,10-trimethylundec-9-enal, 1-(4-Methoxyphenyl)-1-propene, diethylcyclohex-2-en-1-one, dimethylcyclohex-2-en-1-one, Basil comores, 2-methyl-5-(1-methyl-1-ethenyl)-2-cyclohexen-1-one, Cis-3-hexenyl salicylate, methyl 3,3-dimethylbicyclo(2.2.1)heptane-2-carboxylate, Citronellol, Corriander, 2-methyl-3-(4-(1-methylethyl) phenyl)propanal, 1-(2,6,6-trimethyl-1,3-cyclohexadienyl)-2-buten-1-one, Dihydrojasmone, alpha,alpha-Dimethylphenylethylacetate, Dimethyl anthranilate, 1-(2-((1-(ethyloxy)ethyl)oxy)ethyl)benzene, 4-(4-methyl-3-pentenyl)cyclohex-3-ene-1-carbaldehyde, 3-(4-methyl-3-pentenyl)cyclohex-3-ene-1-carbaldehyde), Fir needle, 3-(1,3-benzodioxol-5-yl)-2-methylpropanol, α-ionone, β-ionone, tricyclo[5.2.1.0 2,6]dec-4-en-8-yl ethanoate, Jasmopyrane forte, 1-methoxy-4-(2-propenyl)-benzene, 2-(1,1-dimethylethyl)cyclohexyl ethanoate), PTBCHA, 2,4-dimethyl-4-phenyltetrahydrofuran, 4-Methyl-2-(2-methylprop-1-enyl)tetrahydropyran, Rosemary Tunisian, 3,6-dihydro-2-phenyl-4-methyl-2H-pyran, Terpinolene extra, Tetrahydro linalol, Thyme white, Ti-tree pure, and Undecalactone gamma.

* * * * *

UNITED STATES PATENT AND TRADEMARK OFFICE
CERTIFICATE OF CORRECTION

PATENT NO. : 6,727,221 B1 Page 1 of 1
DATED : April 27, 2004
INVENTOR(S) : Wilson et al.

It is certified that error appears in the above-identified patent and that said Letters Patent is hereby corrected as shown below:

Title page,
Item [22], PCT Filed, change the date to -- July 6, 1999 --

Signed and Sealed this

Fourteenth Day of December, 2004

JON W. DUDAS
*Director of the United States Patent and Trademark Office*